United States Patent
Li et al.

(10) Patent No.: US 11,455,036 B2
(45) Date of Patent: Sep. 27, 2022

(54) CONTROL METHOD OF IGALLERY, CONTROL SYSTEM OF IGALLERY, AND COMPUTER READABLE STORAGE MEDIUM

(71) Applicant: BOE TECHNOLOGY GROUP CO., LTD., Beijing (CN)

(72) Inventors: Wenbo Li, Beijing (CN); Guanshan Tong, Beijing (CN)

(73) Assignee: Beijing BOE Technology Development Co., Ltd., Beijing (CN)

(*) Notice: Subject to any disclaimer, the term of this patent is extended or adjusted under 35 U.S.C. 154(b) by 348 days.

(21) Appl. No.: 16/605,941

(22) PCT Filed: Mar. 18, 2019

(86) PCT No.: PCT/CN2019/078495
§ 371 (c)(1),
(2) Date: Oct. 17, 2019

(87) PCT Pub. No.: WO2019/184745
PCT Pub. Date: Oct. 3, 2019

(65) Prior Publication Data
US 2021/0124418 A1    Apr. 29, 2021

(30) Foreign Application Priority Data

Mar. 30, 2018   (CN) .......................... 201810278095.1

(51) Int. Cl.
G06F 3/01       (2006.01)
A61B 5/374      (2021.01)
A61B 5/378      (2021.01)
A61B 5/16       (2006.01)
G10L 25/63      (2013.01)
G06V 40/20      (2022.01)
(Continued)

(52) U.S. Cl.
CPC .............. *G06F 3/015* (2013.01); *A61B 5/165* (2013.01); *A61B 5/374* (2021.01); *A61B 5/378* (2021.01);
(Continued)

(58) Field of Classification Search
CPC ... G06F 3/015; G06F 2203/011; A61B 5/374; A61B 5/378; A61B 5/165; A61B 5/293;
(Continued)

(56) References Cited

U.S. PATENT DOCUMENTS 10,437,332 B1 * 10/2019 Paterson ............... G06F 40/166
2018/0185609 A1    7/2018 Zhang
(Continued)

FOREIGN PATENT DOCUMENTS

CN      205644515 U     10/2016
CN      106658178 A      5/2017
(Continued)

OTHER PUBLICATIONS

First Office Action and English language translation, CN Application No. 201810278095.1, dated Jul. 2, 2019, 15 pp.
(Continued)

*Primary Examiner* — Kenneth B Lee, Jr.
(74) *Attorney, Agent, or Firm* — Myers Bigel, P.A.

(57) ABSTRACT

This disclosure discloses a control method of iGallery, a control system of iGallery, and a computer readable storage medium. The control method includes determining identity information of a viewer in front of the iGallery, based on a preset target emotion state and the identity information, invoking a pre-stored control instruction corresponding to the identity information in the target emotion state, and controlling the iGallery to correspondingly adjust its display in accordance with the invoked control instruction.

14 Claims, 4 Drawing Sheets

(51) Int. Cl.
*G06V 40/16* (2022.01)
*A61B 5/293* (2021.01)

(52) U.S. Cl.
CPC .......... *G06V 40/172* (2022.01); *G06V 40/174* (2022.01); *G06V 40/20* (2022.01); *G10L 25/63* (2013.01); *A61B 5/293* (2021.01); *G06F 2203/011* (2013.01)

(58) Field of Classification Search
CPC .... G06V 40/174; G06V 40/172; G06V 40/20; G10L 25/63
See application file for complete search history.

(56) References Cited

U.S. PATENT DOCUMENTS

2018/0325441 A1* 11/2018 DeLuca ................ G06F 11/328
2019/0000244 A1* 1/2019 Mu ........................ A47G 1/065

FOREIGN PATENT DOCUMENTS

| | | |
|---|---|---|
| CN | 106874265 A | 6/2017 |
| CN | 106909907 A | 6/2017 |
| CN | 107172337 A | 9/2017 |
| CN | 107320114 A | 11/2017 |
| CN | 107330722 A | 11/2017 |
| CN | 107424019 A | 12/2017 |
| CN | 108549483 A | 9/2018 |

OTHER PUBLICATIONS

Second Office Action and English language translation, CN Application No. 201810278095.1, dated Mar. 26, 2020, 14 pp.

* cited by examiner

CONTROL METHOD OF IGALLERY, CONTROL SYSTEM OF IGALLERY, AND COMPUTER READABLE STORAGE MEDIUM

RELATED APPLICATIONS

The present application is the U.S. national phase entry of PCT/CN2019/078495, with an international filing date of Mar. 18, 2019, which claims the benefit of Chinese Patent Application No. 201810278095.1, filed on Mar. 30, 2018, the entire disclosure of which is incorporated herein by reference.

FIELD OF THE INVENTION

This disclosure relates to the field of display technologies, and in particular to a control method of iGallery, a control system of iGallery, and a computer readable storage medium.

BACKGROUND ART

With the rapid development of economy, more and more families are paying attention to art and culture consumption and pursuing aesthetic expression and realization, but painting and images works are currently the only areas that have not been digitized. IGallery is an emerging family cloud art gallery that includes a featured art content library, an art appreciation and transaction cloud platform, a display terminal capable of restoring original art, and more additional services. With an iGallery product at home, people may enjoy the premium art quality and the high-tech surprises, but there is still a need of user-friendly settings.

SUMMARY

To this end, the embodiments of this disclosure provide a control method of iGallery, a control system of iGallery, and a computer readable storage medium, so as to increase the user-friendly designs of iGallery display.

According to one aspect of this disclosure, a control method of iGallery is provided. The method may comprise determining identity information of a viewer in front of the iGallery; based on a preset target emotion state and the identity information, invoking a pre-stored control instruction corresponding to the identity information in the target emotion state; and controlling the iGallery to correspondingly adjust its display in accordance with the invoked control instruction.

In one embodiment, the method may further comprise determining a current emotion state of the viewer of the same identity information while viewing the adjusted iGallery; determining whether the current emotion state reaches the target emotion state; if not, changing the control instruction corresponding to the identity information based on a plurality of alternative control instructions corresponding to the preset target emotion state, and re-controlling the iGallery to correspondingly adjust its display in accordance with the changed control instruction, so as to determine a current emotion state of the viewer of the same identity information once more; if so, storing the current control instruction as the control instruction corresponding to the identity information.

In one embodiment, determining a current emotion state of the viewer of the same identity information while viewing the adjusted iGallery may comprise: obtaining brain wave information of the viewer; determining a brain wave frequency of the viewer based on the brain wave information; and determining a current emotion state of the viewer according to a preset correspondence between the brain wave band division and the emotion state.

In one embodiment, determining a current emotion state of the viewer of the same identity information while viewing the adjusted iGallery may further comprise: obtaining external morphology information of the viewer; and revising the determined current emotion state of the viewer depending on the external morphology information.

In one embodiment, obtaining external morphology information of the viewer comprises: obtaining facial expression information of the viewer; and/or obtaining sound information of the viewer; and/or obtaining body movement information of the viewer.

In one embodiment, determining identity information of a viewer in front of the iGallery may comprise: obtaining feature information of a viewer in front of the iGallery; determining whether a piece of feature information matching with the feature information of the viewer exists among feature information that has been stored; if so, determining identification information corresponding to the piece of feature information as the identity information of the viewer; if not, assigning new identification information to the piece of feature information and using it as the identity information of the viewer.

In one embodiment, based on a preset target emotion state and the identity information, invoking a pre-stored control instruction corresponding to the identity information in the target emotion state may comprise invoking a pre-stored initial control instruction.

In one embodiment, the initial control instruction is one of a plurality of alternative control instructions corresponding to the preset target emotion state.

According to another aspect of this disclosure, a control system of iGallery is provided. The system may comprise an identity determiner configured for determining identity information of a viewer in front of the iGallery; an instruction invoker configured for invoking, based on a preset target emotion state and the identity information, a pre-stored control instruction corresponding to the identity information in the target emotion state; and a display controller configured for controlling the iGallery to correspondingly adjust its display in accordance with the invoked control instruction.

In one embodiment, the system may further comprise an emotion confirmer configured for determining a current emotion state of the viewer of the same identity information while viewing the adjusted iGallery; a data processor configured for determining whether the current emotion state reaches the target emotion state; a memory configured for storing a current control instruction as the control instruction corresponding to the identity information when it is determined that the current emotion state reaches the target emotion state; and an instruction changer configured for changing the control instruction corresponding to the identity information based on a plurality of alternative control instructions corresponding to the preset target emotion state when it is determined that the current emotion state does not reach the target emotion state; wherein the display controller is further configured for re-controlling the iGallery to correspondingly adjust its display in accordance with the changed control instruction.

In one embodiment, the emotion confirmer may be configured for determining a current emotion state of the viewer of the same identity information at fixed time intervals.

In one embodiment, the emotion confirmer may comprise: an EEG signal collector configured for obtaining brain wave information of the viewer; a signal processor configured for determining a brain wave frequency of the viewer based on the brain wave information; and a data matcher configured for determining a current emotion state of the viewer according to a preset correspondence between the brain wave band division and the emotion state.

In one embodiment, the emotion confirmer may further comprise: an external morphology collector configured for obtaining external morphology information of the viewer; and a data reviser configured for revising the determined current emotion state of the viewer depending on the external morphology information.

In one embodiment, the external morphology collector may comprise: an image capturer configured for obtaining facial expression information of the viewer, and/or obtaining body movement information of the viewer; and/or a sound wave sensor configured for obtaining sound information of the viewer.

According to yet another aspect of this disclosure, a computer readable storage medium is provided. The computer readable storage medium stores computer software instructions which, when executed on a processor, enable the processor to perform the above method.

DETAILED DESCRIPTION OF EMBODIMENTS

To render the goals, the technical solutions and the advantages of this disclosure clearer, this disclosure will be further described in detail with reference to the drawings. Obviously, the described embodiments are only part of the embodiments of this disclosure, but not all embodiments. Based on the embodiments in this disclosure, all other embodiments obtainable by a person having ordinary skills in the art without any inventive efforts shall fall within the protection scope of this disclosure.

Figure 1:
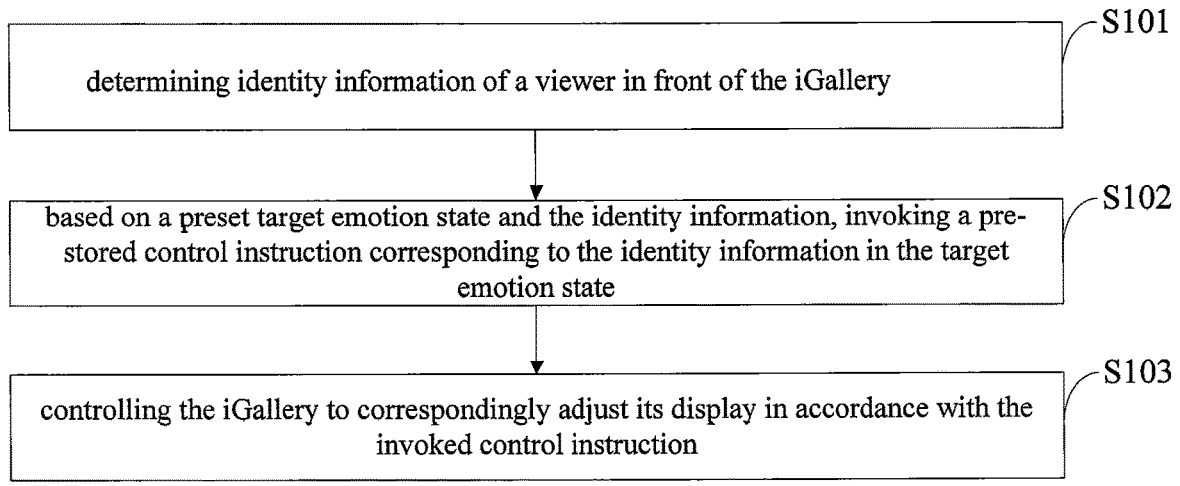
FIG. 1 is a flow chart of a control method of iGallery provided in an embodiment of this disclosure.

FIG. 1 is a flow chart of a control method of iGallery provided in an embodiment of this disclosure. As shown in FIG. 1, the method may comprise:

S101, determining identity information of a viewer in front of the iGallery;

S102, based on a preset target emotion state and the identity information, invoking a pre-stored control instruction corresponding to the identity information in the target emotion state;

S103, controlling the iGallery to correspondingly adjust its display in accordance with the invoked control instruction.

By identifying identity information of different viewers and invoking a pre-stored control instruction corresponding to the identity information in a target emotion state, the control method of iGallery provided in the embodiments of this disclosure controls the iGallery to correspondingly adjust its display and achieves the effect of using the display information of the iGallery to accurately adjust the emotion states of the viewers to reach the target emotion state such that the iGallery is more user-friendly.

In one embodiment, the target emotion state may be specifically set upon an application scene of the iGallery. For example, in a quiet office location, the target emotion state may be soothing and calm, so that the emotion state of the viewer tends to be soothing and calm upon watching the display information of the iGallery, which is good for work. Another example is that, in a memorial meeting, the target emotion state may be sad, so that the emotion state of the viewer tends to sadness upon watching the display information of the iGallery, thereby conforming to the current scene.

In actual applications, the same iGallery may be used by a plurality of viewers and the emotion states of different viewers will change differently responsive to the same display information. Therefore, when adjusting the display of the iGallery, pertinent adjustment should be performed with respect to different viewers. Based on that, in the control method provided in the embodiments of this disclosure, firstly, it is necessary to execute step S101 to determine identity information of the current viewer in front of the iGallery.

The current viewer may be a viewer who uses the iGallery for the first time, or a viewer who has already used it before. For a viewer who uses the iGallery for the first time, it is necessary to configure identification information corresponding to the viewer, so as to facilitate subsequent identity identification. For a viewer who has already used the iGallery before, it is necessary to identify the identification information corresponding to the current viewer among the identification information that has been stored.

Based on that, in the control method of iGallery provided in the embodiments of this disclosure, step S101 of determining identity information of the current viewer in front of the iGallery may comprise:

Firstly, obtaining feature information, e.g., facial feature information, of the viewer in front of the iGallery;

After that, determining whether a piece of feature information matching with the feature information of the viewer exists among feature information that has been stored;

If so, determining identification information corresponding to the piece of feature information as the identity information of the viewer;

If not, assigning new identification information to the piece of feature information and using it as the identity information of the viewer.

In the control method of iGallery provided in the embodiments of this disclosure, for a specified target emotion state, a plurality of alternative control instructions corresponding to the target emotion state are pre-stored, and each alternative control instruction is used for controlling the iGallery to correspondingly adjust its display. Different alternative control instructions control different display adjustments. In one embodiment, for the target emotion state, an alternative control instruction may be preset as an initial control instruction from a plurality of alternative control instructions. In this case, the initial control instruction corresponds to the target emotion state. Therefore, for all newly assigned identification information (i.e., all new identity information), they (the new identity information) correspond to one and the same initial control instruction. For example, if the specified target emotion state is soothing, the alternative control instructions may comprise: a control instruction corresponding to changing the background picture information to green, a control instruction corresponding to changing the brightness of the picture, a control instruction corresponding to displaying family picture information, a control instruction corresponding to displaying some beautiful sceneries such as a vast grassland, boundless sea, high mountains, a gurgling stream or the like.

For a viewer who uses the iGallery for the first time, his or her identity information is newly assigned identification information and there is no alternative control instruction corresponding to the newly assigned identification information pre-stored in the memory. For example, step S102 of invoking, based on a preset target emotion state and the identity information, a pre-stored control instruction corresponding to the identity information in the target emotion state may comprise invoking a pre-stored initial control instruction in the target emotion state as the control instruction corresponding to the identity information. For a viewer who has already used the iGallery, since an alternative control instruction corresponding to his/her identity information has been pre-stored in the memory, the pre-stored alternative control instruction corresponding to his/her identity information in the target emotion state may be invoked directly. In this case, the invoked control instruction may be the initial control instruction or other alternative control instructions corresponding to the target emotion state.

Figure 2:
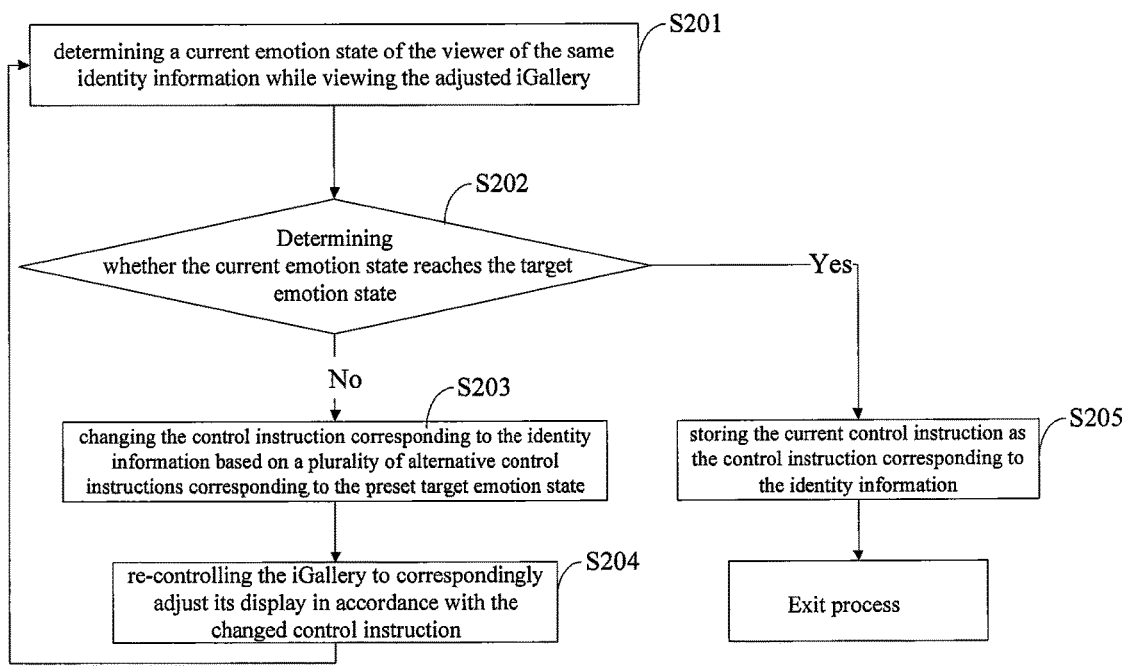
FIG. 2 is optional subsequent steps of the control method of iGallery shown in FIG. 1.

In the control method of iGallery provided in the embodiments of this disclosure, after the execution of step S103 of controlling the iGallery to correspondingly adjust its display in accordance with the invoked control instruction, the emotion state of the viewer of the same identity information may vary with the picture information that is viewed, e.g., from frustration to relaxation, from anger to sadness, or from relaxation to sadness. In order that the current emotion state of the same viewer better conforms to the target emotion state, the control instruction corresponding to the identity information of the same viewer in the target emotion state may be revised continuously. Therefore, the control method of iGallery provided according to the embodiments of this disclosure may further comprise optional subsequent steps shown in FIG. 2 based on the method of FIG. 1. FIG. 2 is optional subsequent steps of the control method of iGallery shown in FIG. 1. FIG. 2 is merely an example of implementing control instruction revision by self-learning. After step S103 shown in FIG. 1, the method may further comprise the following steps shown in FIG. 2:

S201, determining a current emotion state of the viewer of the same identity information while viewing the adjusted iGallery;

S202, determining whether the current emotion state reaches the target emotion state; if not, executing step S203; if so, executing step 205;

S203, changing the control instruction corresponding to the identity information based on a plurality of alternative control instructions corresponding to the preset target emotion state;

S204, re-controlling the iGallery to correspondingly adjust its display in accordance with the changed control instruction; after that, returning to step S201;

S205, storing the current control instruction as the control instruction corresponding to the identity information.

As shown in FIG. 2, after step S205, the control method may end.

By continuously repeating the above steps S201 to S204 in a loop, the control instruction corresponding to the identity information in the target emotion state may be continuously revised, so that the emotion state of the viewer corresponding to the identity information may be effectively adjusted to reach the target emotion state.

In one embodiment, in the above control method provided in the embodiments of this disclosure, the step S202 of determining whether the current emotion state reaches the target emotion state may comprise: determining whether the current emotion state is consistent with the target emotion state, or falls within a target range of the target emotion state. For example, the target emotion state is soothing. In this case, if the current emotion state is detected to be relaxed or joyful, it means that the current emotion state has reached the target emotion state, and there is no need to adjust the display information of the iGallery any more, i.e., the current display information of the iGallery will be retained.

In one embodiment, in the control method provided in the embodiments of this disclosure, step S203 of changing the control instruction corresponding to the identity information based on a plurality of alternative control instructions corresponding to the preset target emotion state may comprise: selecting randomly or sequentially, from the plurality of alternative control instructions, an alternative control instruction different from the current control instruction corresponding to the identity information, and using it as a changed control instruction corresponding to the identity information.

In the control method provided in the embodiments of this disclosure, step S201 of determining a current emotion state of the viewer of the same identity information while viewing the adjusted iGallery may be preceded by step S103 of controlling the iGallery to correspondingly adjust its display, or step S204 of re-controlling the iGallery to correspondingly adjust its display, and executed at fixed time intervals, e.g., after 5 minutes, so as to spare sufficient time for changes in the emotion state of the viewer.

Figure 3:
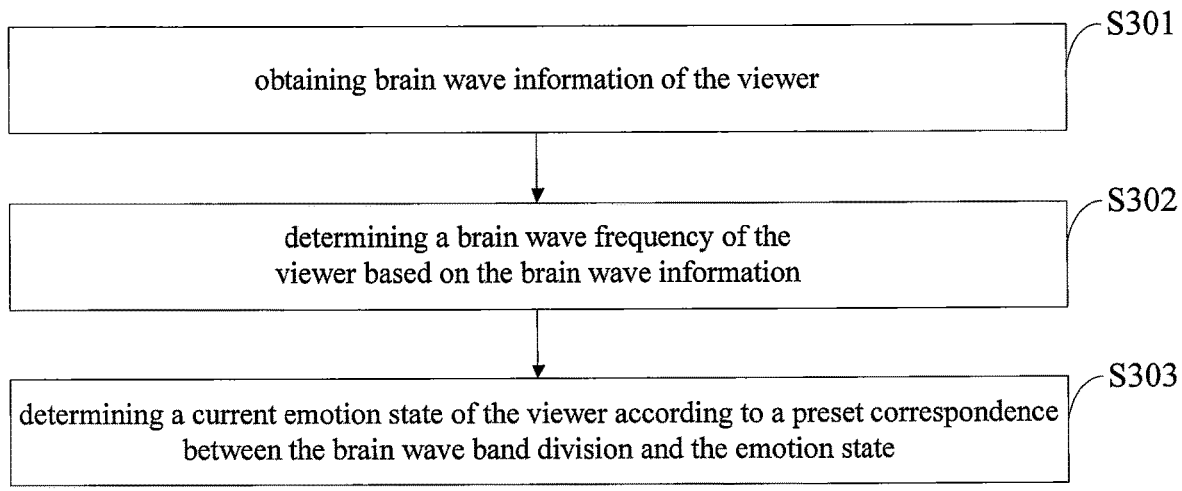
FIG. 3 is an embodiment of step S201 shown in FIG. 2.

FIG. 3 is an embodiment of step S201 shown in FIG. 2. As shown in FIG. 3, step S201 of determining a current emotion state of the viewer of the same identity information while viewing the adjusted iGallery may comprise:

S301, obtaining brain wave information of the viewer;

S302, determining a brain wave frequency of the viewer based on the brain wave information;

S303, determining a current emotion state of the viewer according to a preset correspondence between the brain wave band division and the emotion state.

The brain wave information of the viewer varies with the mood, i.e., the inner activity, of the viewer. Various waveform information of the brain waves may be obtained in an intuitional manner from step S301. A brain wave frequency of the viewer may be obtained through algorithm analysis of the waveform information of the brain waves in step S302. As may be seen from table 1 below, different brain wave bands correspond to different emotion states of the viewer. Therefore, we may preset a correspondence between the brain wave band and the emotion state, and then determine a current emotion state of the viewer according to the determined brain wave frequency of the viewer.

For example, when the brain wave frequency of the viewer is detected to belong to Beta band to B band, it may be determined that the emotion of the viewer is very tense. When the brain wave frequency of the viewer is detected to belong to AlPha band to A band, it may be determined that the viewer is in a relaxed state.

TABLE 1

| | Frequency (HZ) | State |
|---|---|---|
| δ | 0.5-2.75 | A sleeping state, which occurs when a person is in a deep sleep without dreams, and is sometimes found in an experienced thinker. |
| θ | 3.5-6.75 | A deep relaxation state; a light sleep state, also called a contemplation or meditation state, a subconscious state. The subconsciousness is subjected to hints; creativity and inspiration burst out; the person is perceptive and intuitional; studies and memories are accelerated. An ordinary person may only adjust himself/herself to θ waves consciously after long term training. |
| α | 7.5-9.25 | A relaxed state, in which the brain is sober and |
| A | 10-11.75 | relaxed, and may readily concentrate on learning and working without being disturbed or easily getting tired. An ordinary person may only adjust himself/herself to α waves consciously after long term training. |
| β | 13-16.75 | A tense state, in which a person is sensitive to the |
| B | 18-29.75 | ambience so that he/she may not concentrate and easily gets tired. Most people are in such a state when they are sober. |
| γ | 31-39.75 | A frequency unbearable for an ordinary person, |
| Γ | 41-49.75 | which only occurs as an outpouring in short terms. In this case, a focus of high creativity and insights may be found, and a person in meditation may feel entering the realm of Nirvana. |

Figure 4:
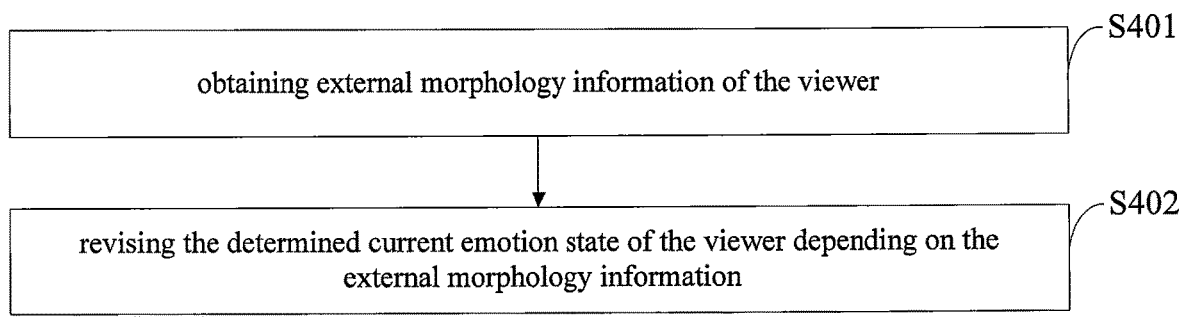
FIG. 4 is optional subsequent steps of the embodiment of step S201 shown in FIG. 3.

In the control method provided in the embodiments of this disclosure, since there is a certain deviation when judging the emotion of the viewer based on the brain wave information only, step S201 may further comprise steps shown in FIG. 4 based on the steps shown in FIG. 3, thereby revising the determined current emotion state such that the determined current emotion state is more accurate.

FIG. 4 is optional subsequent steps of the embodiment of step S201 shown in FIG. 3. After step S303, as shown in FIG. 4, step S201 of determining a current emotion state of the viewer of the same identity information while viewing the adjusted iGallery may comprise:

S401, obtaining external morphology information of the viewer;

S402, revising the determined current emotion state of the viewer depending on the external morphology information.

The external morphology information of the viewer obtained from step S401 may reflect the emotion state of the viewer in an intuitional manner. The brain wave information may be complemented by the external morphology information, and similar emotions may be identified accurately, which renders the determined current emotion state of the viewer more accurate. For example, if the current emotion state of the viewer determined based on the brain wave information is a relaxed state, and meanwhile the obtained external morphology information is that the viewer is smiling, the current emotion state of the viewer may be further refined as a joyful state.

In the control method provided in the embodiments of this disclosure, there may be various external morphology information reflecting the emotion state of the viewer, such as facial expression of a person, body language of a person, conversation volume and voice frequency of a person. Based on that, step S401 of obtaining external morphology information of the viewer may comprise:

Obtaining facial expression information of the viewer, and specifically obtaining facial expression information of the viewer with an image acquisition device such as a camera, e.g., obtaining the information that the face of the viewer is in a crying state; and/or Obtaining sound information of the viewer, and specifically obtaining volume and voice frequency information of the viewer with a device like a microphone or a sound wave sensor, e.g., obtaining the information that the volume of viewer is large and the voice frequency of the viewer is high; and/or Obtaining body movement information of the viewer, and specifically, obtaining body movement language of the viewer with a device like an infrared sensor or a camera, e.g., obtaining the information that the body of the viewer is in a state of fast movement.

Figure 5:
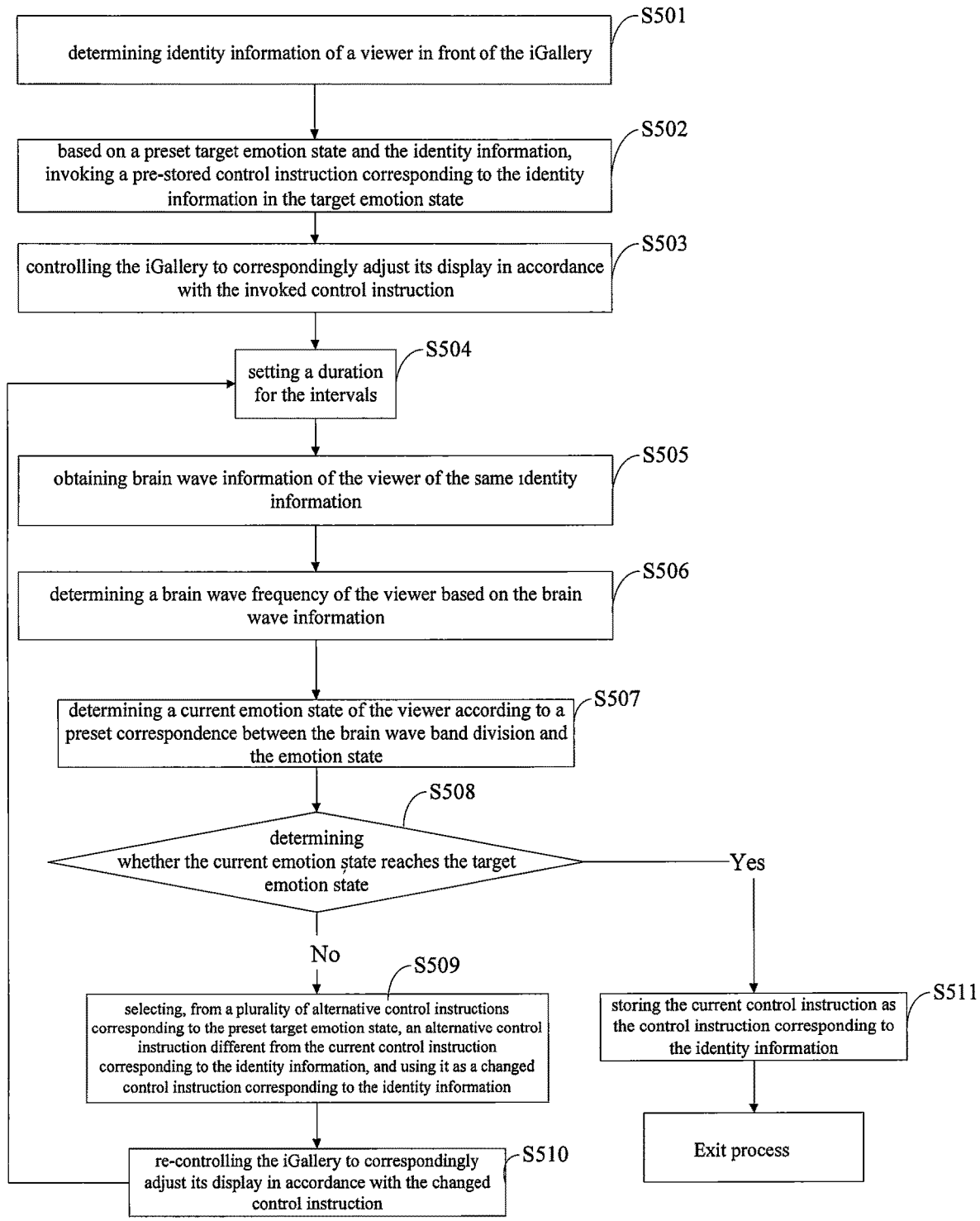
FIG. 5 is a further flow chart of the control method of iGallery provided in an embodiment of this disclosure.

The current emotion state of the viewer may be accurately identified by obtaining various specific external morphology information in combination with the brain wave information. FIG. 5 is a further flow chart of the iGallery control method provided in an embodiment of this disclosure. As shown in FIG. 5, the control method may comprise steps of:

S501, determining identity information of a viewer in front of the iGallery;

S502, based on a preset target emotion state and the identity information, invoking a pre-stored control instruction corresponding to the identity information in the target emotion state;

S503, controlling the iGallery to correspondingly adjust its display in accordance with the invoked control instruction;

S504, setting a duration for the intervals, e.g., 5 minutes;

S505, obtaining brain wave information of the viewer of the same identity information;

S506, determining a brain wave frequency of the viewer based on the brain wave information;

S507, determining a current emotion state of the viewer according to a preset correspondence between the brain wave band division and the emotion state;

S508, determining whether the current emotion state reaches the target emotion state; if not, executing step S509; if so, executing step 511;

S509, selecting, from a plurality of alternative control instructions corresponding to the preset target emotion state, an alternative control instruction different from the current control instruction corresponding to the identity information, and using it as a changed control instruction corresponding to the identity information;

S510, re-controlling the iGallery to correspondingly adjust its display in accordance with the changed control instruction; after that, returning to step S504;

S511, storing the current control instruction as the control instruction corresponding to the identity information.

After step S511, the control method may end.

Based on the same inventive concept, the embodiments of this disclosure further provide an control system of iGallery. Since the principle of the system for solving problems is similar to that of the iGallery control method mentioned above, the implementation of the system may refer to the implementation of the control method, which will not be repeated for simplicity.

Figure 6:
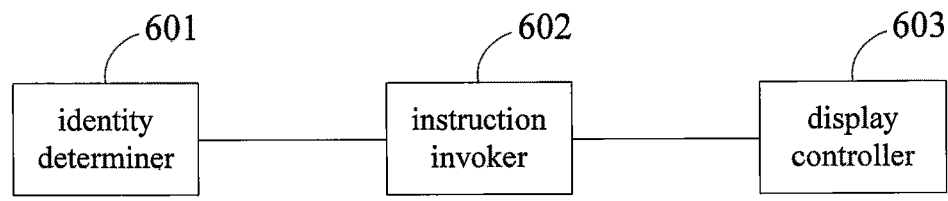
FIG. 6 is a schematic structure view of a control system of iGallery provided in an embodiment of this disclosure.

FIG. 6 is a schematic structure view of a control system of iGallery provided in an embodiment of this disclosure. As shown in FIG. 6, the control system may comprise:

an identity determiner 601 configured for determining identity information of a viewer in front of the iGallery;

an instruction invoker 602 configured for invoking, based on a preset target emotion state and the identity information, a pre-stored control instruction corresponding to the identity information in the target emotion state;

a display controller 603 configured for controlling the iGallery to correspondingly adjust its display in accordance with the invoked control instruction.

In one embodiment, the identity determiner 601, the instruction invoker 602 and the display controller 603 may be integrated in the iGallery at the same time. In another embodiment, the instruction invoker 602 and the display controller 603 may be integrated in the iGallery at the same time, while the identity determiner 601 may be arranged separately in a device outside the iGallery. In yet another embodiment, the display controller 603 may be integrated in the iGallery, while the identity determiner 601 and the instruction invoker 602 may be arranged in a device outside the iGallery. This is not limited herein.

Figure 7:
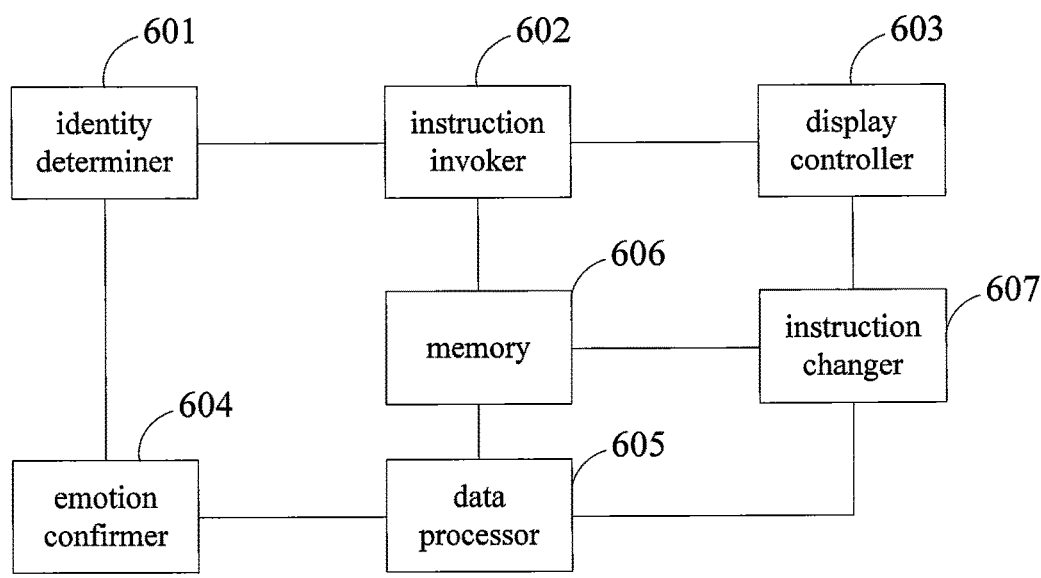
FIG. 7 is a further schematic structure view of the control system of iGallery provided in an embodiment of this disclosure.

FIG. 7 is a further schematic structure view of a control system of iGallery provided in an embodiment of this disclosure. In addition to the various components (i.e., the identity determiner 601, the instruction invoker 602 and the display controller 603) shown in FIG. 6, the control system shown in FIG. 7 may further comprise:

an emotion confirmer 604 configured for determining a current emotion state of the viewer of the same identity information while viewing the adjusted iGallery;

a data processor 605 configured for determining whether the current emotion state reaches the target emotion state;

a memory 606 configured for storing a current control instruction as the control instruction corresponding to the identity information when it is determined that the current emotion state reaches the target emotion state; and an instruction changer 607 configured for changing the control instruction corresponding to the identity information based on a plurality of alternative control instructions corresponding to the preset target emotion state when it is determined that the current emotion state does not reach the target emotion state.

In one embodiment, in addition to being configured for controlling the iGallery to correspondingly adjust its display in accordance with the invoked control instruction, the display controller 603 may be further configured for re-controlling the iGallery to correspondingly adjust its display in accordance with the changed control instruction.

According to this disclosure, the emotion confirmer 604 may be configured for determining a current emotion state of the viewer of the same identity information at fixed time intervals (e.g., every 5 minutes). In this way, the emotion confirmer 604, the data processor 605, the instruction changer 607, the memory 606 and the display controller 603 form a cycle in which related operations are performed according to the aforementioned logical loop until the data processor 605 determines that the current emotion state of the viewer of the same identity information reaches the target emotion state.

Figure 8:
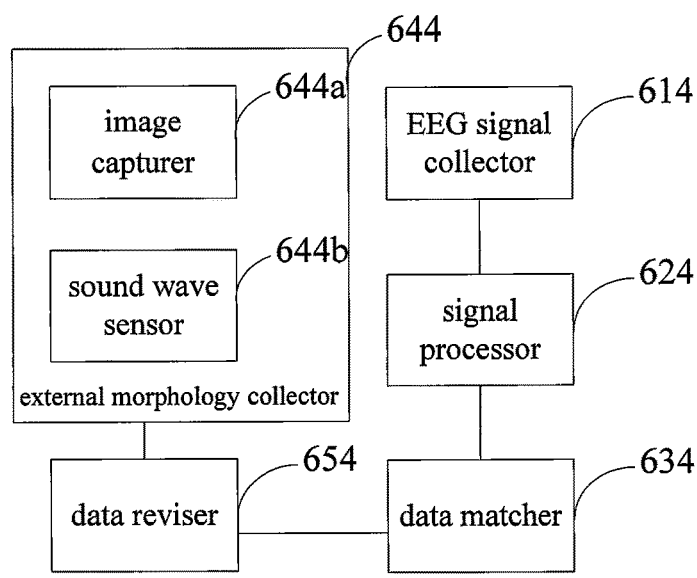
FIG. 8 is an embodiment of an emotion confirmer of the control system shown in FIG. 7.

FIG. 8 is an embodiment of the emotion confirmer 604 of the control system shown in FIG. 7. As shown in FIG. 8, the emotion confirmer 604 may comprise:

an EEG signal collector 614 configured for obtaining brain wave information of the viewer;

a signal processor 624 configured for determining a brain wave frequency of the viewer based on the brain wave information;

a data matcher 634 configured for determining a current emotion state of the viewer according to a preset correspondence between the brain wave band division and the emotion state.

In one embodiment, the EEG signal collector 614 may comprise an external electrode or an internal electrode embedded in the cerebral cortex, which will not be limited in this disclosure.

In the control system provided in the embodiments of this disclosure, as shown in FIG. 8, the emotion confirmer 604 may further comprise:

an external morphology collector 644 configured for obtaining external morphology information of the viewer;

a data reviser 654 configured for revising the determined current emotion state of the viewer depending on the external morphology information.

In the control system provided in the embodiments of this disclosure, as shown in FIG. 8, the external morphology collector 644 may comprise:

an image capturer 644a configured for obtaining facial expression information of the viewer, and/or obtaining body movement information of the viewer; and/or a sound wave sensor 644b configured for obtaining sound information of the viewer.

The image capturer 644a may be a camera.

The embodiments of this disclosure further provide a computer readable storage medium which stores computer software instructions which, when executed on a processor, enable the processor to perform the iGallery control method mentioned above.

From the depictions of the above implementation, those skilled in the art can clearly understand that the embodiments of this disclosure may be implemented by means of hardware, or by means of software in combination with a necessary universal hardware platform. Based on the above understanding, the technical solution of the embodiments of this disclosure may be embodied in the form of a software product, which may be stored in a non-volatile storage medium (which may be a CD-ROM, a U-disk, a mobile hard disk, etc.), and includes several instructions for enabling a computer device (which may be a personal computer, a server, or a network device, etc.) to perform the method of each embodiment of this disclosure.

Those skilled in the art can understand that the drawings are only schematic views of preferred embodiments, and the modules or processes in the drawings are not necessarily essential for the implementation of this disclosure.

Those skilled in the art can understand that modules in an apparatus of an embodiment may be distributed in the apparatus of the embodiment as described in the embodiment, or be modified correspondingly to be in one or more apparatuses different from the embodiment. The modules in the above embodiment may be combined as one module, or further split into a plurality of sub-modules.

The serial numbers of the embodiments of this disclosure are merely provided for descriptive purposes, and do not represent superiority or inferiority of the embodiments.

By identifying identity information of different viewers and invoking a pre-stored control instruction corresponding to the identity information in a target emotion state, the iGallery control method and control system and the computer readable storage medium provided in the embodiments of this disclosure control the iGallery to correspondingly adjust its display and achieve the effect of using the display information of the iGallery to accurately adjust the emotion states of the viewers to reach the target emotion state such that the iGallery is more user-friendly.

Obviously, those skilled in the art can make various modifications and variations to this disclosure without departing from spirits and scopes of this disclosure. Thus if these modifications and variations to this disclosure fall within the scopes of the claims of this disclosure and the equivalent techniques thereof, this disclosure is intended to include them too.

The invention claimed is:

1. A control method of an iGallery, comprising:
   determining identity information of a viewer in front of the iGallery;
   based on a preset target emotion state and the identity information, invoking a pre-stored control instruction corresponding to the identity information in the target emotion state; and
   controlling the iGallery to correspondingly adjust a display of the iGallery in accordance with the control instruction that was invoked,
   wherein the determining identity information of the viewer in front of the iGallery comprises:
   obtaining feature information of the viewer in front of the iGallery;
   determining whether a piece of feature information matching with the feature information of the viewer exists among feature information that has been stored;
   responsive to the piece of feature information matching with the feature information of the viewer existing among the feature information that has been stored, determining identification information corresponding to the piece of feature information as the identity information of the viewer; and
   responsive to the piece of feature information not matching with the feature information of the viewer existing among the feature information that has been stored, assigning new identification information to the piece of feature information and using the new identification information as the identity information of the viewer.

2. The control method according to claim 1, further comprising:
   determining a current emotion state of the viewer of a same identity information while viewing the iGallery that was adjusted;
   determining whether the current emotion state reaches the target emotion state;
   responsive to the current emotion state not reaching the target emotion state, changing the control instruction corresponding to the identity information based on a plurality of alternative control instructions corresponding to the preset target emotion state, and re-controlling the iGallery to correspondingly adjust the display in accordance with the control instruction that was changed, to determine a current emotion state of the viewer of the same identity information once more; and
   responsive to the current emotion state reaching the target emotion state, storing a current control instruction as the control instruction corresponding to the identity information.

3. The control method according to claim 2, wherein the determining the current emotion state of the viewer of the same identity information while viewing the iGallery that was adjusted comprises:
   obtaining brain wave information of the viewer;
   determining a brain wave frequency of the viewer based on the brain wave information; and
   determining the current emotion state of the viewer according to a preset correspondence between a brain wave band division and the current emotion state.

4. The control method according to claim 3, wherein the determining the current emotion state of the viewer of the same identity information while viewing the iGallery that was adjusted further comprises:
   obtaining external morphology information of the viewer; and
   revising the current emotion state of the viewer that was determined depending on the external morphology information.

5. The control method according to claim 4, wherein the obtaining external morphology information of the viewer comprises:
   obtaining facial expression information of the viewer; and/or
   obtaining sound information of the viewer; and/or
   obtaining body movement information of the viewer.

6. The control method according to claim 1, wherein the invoking the pre-stored control instruction corresponding to the identity information in the target emotion state comprises:
   invoking a pre-stored initial control instruction.

7. The control method according to claim 6, wherein the initial control instruction is one of a plurality of alternative control instructions corresponding to the preset target emotion state.

8. A control system of an iGallery, comprising:
   an identity determiner configured for determining identity information of a viewer in front of the iGallery;
   an instruction invoker configured for invoking, based on a preset target emotion state and the identity information, a pre-stored control instruction corresponding to the identity information in the target emotion state; and
   a display controller configured for controlling the iGallery to correspondingly adjust a display of the iGallery in accordance with the control instruction that was invoked,
   wherein the identity determiner is further configured for:
   obtaining feature information of the viewer in front of the iGallery;
   determining whether a piece of feature information matching with the feature information of the viewer exists among feature information that has been stored;
   responsive to the piece of feature information matching with the feature information of the viewer existing among the feature information that has been stored, determining identification information corresponding to the piece of feature information as the identity information of the viewer; and
   responsive to the piece of feature information not matching with the feature information of the viewer existing among the feature information that has been stored, assigning new identification information to the piece of feature information and using the new identification information as the identity information of the viewer.

9. The control system according to claim 8, further comprising:
   an emotion confirmer configured for determining a current emotion state of the viewer of a same identity information while viewing the iGallery that was adjusted;
   a data processor configured for determining whether the current emotion state reaches the target emotion state;
   a memory configured for storing a current control instruction as the control instruction corresponding to the identity information responsive to determining that the current emotion state reaches the target emotion state; and
   an instruction changer configured for changing the control instruction corresponding to the identity information based on a plurality of alternative control instructions corresponding to the preset target emotion state responsive to determining that the current emotion state does not reach the target emotion state, wherein the display controller is configured for re-controlling the iGallery to correspondingly adjust the display in accordance with the control instruction that was changed.

10. The control system according to claim 9, wherein the emotion confirmer is configured for determining a current emotion state of the viewer of the same identity information at fixed time intervals.

11. The control system according to claim 9, wherein the emotion confirmer comprises:
    an EEG signal collector configured for obtaining brain wave information of the viewer;
    a signal processor configured for determining a brain wave frequency of the viewer based on the brain wave information; and
    a data matcher configured for determining the current emotion state of the viewer according to a preset correspondence between a brain wave band division and the current emotion state.

12. The control system according to claim 11, wherein the emotion confirmer further comprises:
    an external morphology collector configured for obtaining external morphology information of the viewer; and
    a data reviser configured for revising the current emotion state of the viewer that was determined depending on the external morphology information.

13. The control system according to claim 12, wherein the external morphology collector comprises:
    an image capturer configured for obtaining facial expression information of the viewer, and/or obtaining body movement information of the viewer; and/or
    a sound wave sensor configured for obtaining sound information of the viewer.

14. A non-transitory computer readable storage medium that stores computer software instructions which, when executed on a processor, enable the processor to perform the method according to claim 1.

* * * * *